United States Patent
Vaghefi

(10) Patent No.: US 6,541,030 B2
(45) Date of Patent: Apr. 1, 2003

(54) INSTANT WATER DISSOLVABLE ENCAPSULATE AND PROCESS

(75) Inventor: Farid Vaghefi, Exton, PA (US)

(73) Assignee: Verion Inc., Lionville, PA (US)

( * ) Notice: Subject to any disclaimer, the term of this patent is extended or adjusted under 35 U.S.C. 154(b) by 0 days.

(21) Appl. No.: 09/964,163

(22) Filed: Sep. 26, 2001

(65) Prior Publication Data

US 2002/0037321 A1 Mar. 28, 2002

Related U.S. Application Data

(60) Provisional application No. 60/235,754, filed on Sep. 27, 2000.

(51) Int. Cl.⁷ .................................................. A61K 9/48
(52) U.S. Cl. ...................................... 424/451; 424/401
(58) Field of Search ............................... 424/400, 451; 426/89, 658; 428/402; 512/4

(56) References Cited

U.S. PATENT DOCUMENTS

| | | | |
|---|---|---|---|
| 3,080,293 A | 3/1963 | Koff | 167/81 |
| 3,455,838 A | 7/1969 | Marotta et al. | 252/316 |
| 3,499,962 A | 3/1970 | Wurzburg et al. | 424/35 |
| 3,565,819 A | 2/1971 | Gragger | 252/316 |
| 3,664,963 A | 5/1972 | Pasin | 252/316 |
| 3,949,094 A | 4/1976 | Johnson et al. | 426/99 |
| 4,131,648 A | 12/1978 | Choi et al. | 424/22 |
| 4,146,499 A | 3/1979 | Rosano | 252/186 |
| 4,182,778 A | 1/1980 | Hall et al. | 426/72 |
| 4,276,312 A * | 6/1981 | Merritt | 426/96 |
| 4,353,962 A | 10/1982 | Himel et al. | 428/407 |
| 4,380,555 A | 4/1983 | Campagne et al. | 426/549 |
| 4,389,419 A | 6/1983 | Lim et al. | 426/72 |
| 4,479,911 A | 10/1984 | Fong | 264/4.6 |
| 4,490,407 A | 12/1984 | Lafon | 427/2 |
| 4,540,602 A | 9/1985 | Motoyama et al. | 427/213.31 |
| 4,891,223 A | 1/1990 | Ambegaonkar et al. | 424/408 |
| 4,978,483 A | 12/1990 | Redding, Jr. | 264/4.32 |
| 5,209,879 A | 5/1993 | Redding, Jr. | 264/23 |
| 5,213,810 A | 5/1993 | Steber | 424/490 |
| 5,252,337 A | 10/1993 | Powell | 424/456 |
| 5,271,881 A | 12/1993 | Redding, Jr. | 264/432 |
| 5,317,004 A | 5/1994 | Misselbrook et al. | 504/116 |
| 5,370,881 A | 12/1994 | Fuisz | 426/5 |
| 5,407,609 A | 4/1995 | Tice et al. | 264/46 |
| 5,455,342 A | 10/1995 | Redding, Jr. | 536/102 |
| 5,460,756 A | 10/1995 | Redding, Jr. | 264/4 |
| 5,482,702 A | 1/1996 | Murphy et al. | 424/65 |
| 5,601,760 A | 2/1997 | Rosenberg | 264/4.1 |
| 5,614,179 A | 3/1997 | Murphy et al. | 424/65 |
| 5,643,607 A | 7/1997 | Okada et al. | 424/493 |
| 5,651,990 A | 7/1997 | Takada et al. | 424/497 |
| 5,783,211 A | 7/1998 | Manzo | 424/450 |
| 5,814,342 A | 9/1998 | Okada et al. | 424/493 |
| 5,916,596 A | 6/1999 | Desai et al. | 424/489 |
| 5,925,381 A | 7/1999 | Boyle et al. | 424/499 |
| 5,945,085 A | 8/1999 | Salas et al. | 424/45 |
| 5,955,036 A | 9/1999 | Seyffert et al. | 422/139 |
| 5,976,575 A | 11/1999 | Gellenbeck | 424/489 |
| 5,980,942 A | 11/1999 | Katzhendler et al. | 424/465 |
| 5,989,583 A | 11/1999 | Amselem | 424/439 |
| 6,001,346 A | 12/1999 | Delwiche et al. | 424/84 |
| 6,015,546 A | 1/2000 | Sutton et al. | 424/9.52 |
| 6,017,513 A | 1/2000 | Betbeder et al. | 424/1.73 |
| 6,045,835 A | 4/2000 | Soper et al. | 426/89 |

* cited by examiner

*Primary Examiner*—Michael G. Hartley
*Assistant Examiner*—Konata M. George
(74) *Attorney, Agent, or Firm*—Synnestvedt & Lechner LLP

(57) ABSTRACT

A microcapsule capable of thoroughly encapsulating environmentally-sensitive or volatile core materials and capable of releasing said core material on contact with water. A process for manufacture of water soluble microcapsules comprising the admixture of a water soluble cellulosic material, a water soluble glucopyranosidyl material, at least two surfactants and core material, subjecting said mixture to an abrupt pressure change and drying the pressure-treated mixture.

30 Claims, No Drawings

INSTANT WATER DISSOLVABLE ENCAPSULATE AND PROCESS

The application claims the benefit of U.S. Provisional Application No. 60/235,754, filed Sep. 27, 2000.

FIELD OF THE INVENTION

The present invention relates to water soluble microcapsule compositions, processes for their preparation and their uses in various applications including the food, nutriceutical and pharmaceutical industries.

BACKGROUND OF THE INVENTION

Capsules have been developed to serve a variety of functions. One general purpose of encapsulation is to preserve or isolate the core material from its environment until an appropriate time or condition is present. In these situations, the core material is protected from the environment by the shell. Such protection is not always easily achieved since the core material may be able to penetrate or diffuse through the shell. On the other hand, use can be made of the "leaky" feature of some shells to control the release rate of the core material into the surrounding environment.

Encapsulation can protect compounds from environmental conditions such as temperature, pH, or chemically reactive surroundings such as oxidizing and reducing environments. Such oxidizing and reducing environments may consist of chemicals to which the capsule has been added. In other cases, it is desirable to encapsulate certain chemical compounds not only for protection of the core but also to protect or shield the external environment from reaction with the chemical compound forming the core. One common example of this use for encapsulation is the masking of the taste and/or odor of a chemical composition. In such a case, encapsulation may offer protection against detection of a bitter, toxic or otherwise undesirable taste or odor. Encapsulation of skin and respiratory irritants and toxins is one important way to protect the handlers of such materials from exposure.

A variety of micro-encapsulation methods and compositions are known in the art. These compositions are primarily used in food, agricultural and pharmaceutical formulations, for example, to flavor products, to mask the taste of bitter drugs, formulate prolonged dosage forms, separate incompatible materials, protect chemicals from moisture or oxidation, or modify the physical characteristics of the material for ease of handling and/or processing.

Many liquids, such as flavors and fragrance oils for example, contain a mixture of volatile alcohols and aromatics, which evaporate when exposed to even minimal heat. Indeed, many such substances often lose as much as 45% of their original weight during the encapsulation process due to volatilization. Such losses are wasteful and expensive. Additionally, resulting end-products of these methods often taste less poignant or smell less desirable than the original liquids.

Many of the techniques used to microencapsulate involve the polymerization or setting of a resin, such as a polyurea, to form the outer shell of the microsphere. Typical pharmaceutical encapsulation compositions include, e.g., gelatin, polyvinyl alcohol, ethylcellulose, cellulose acetatephthalate and styrene maleic anhydride. See Remington's Pharmaceutical Sciences, Mack Publishing Co., Easton Pa. (1990). Other techniques use primarily fats, waxes or polymers to film form the outer shell.

The use of fats as a retention media for volatiles is disclosed in U.S. Pat. No. 3,949,094 of Johnson, et al. issued Apr. 6, 1976, wherein volatile flavorings, seasonings, colorants, flavor enhancers and the like are blended with lipoidal material under super atmospheric conditions for subsequent handling or conversion into particulates by a spray chilling process. While retention of the volatiles within fat under pressure reduces vaporization before processing, excessive losses are still experienced during the Johnson spray chilling encapsulation method.

Redding, U.S. Pat. No. 5,460,756 describes the entrapping of liquids within a stable lipid or wax shell using pressure pulse techniques.

Lim, et al., U.S. Pat. No. 4,389,419 describes the formation of an emulsion consisting of a continuous phase aqueous solution of an alkali metal alginate, and optionally, water-soluble alcohol-insoluble filler such as a polysaccharide, and a dispersed phase of an oleophilic substance. The emulsion thus produced is then formed into droplets, which are immersed into an alcoholic solution of multi-valent cations, to produce a water-insoluble shape-retaining alginate matrix filled with precipitated polysaccharide and enclosing plural oil droplets.

Another markedly different approach employed for encapsulating vitamin or mineral nutrients, such as thiamine, is described by Hall, et al., U.S. Pat. No. 4,182,778 issued Jan. 8, 1980. Hall, et al. describe encapsulation by fluidizing the nutrient in a gaseous stream and contacting the nutrient with finely atomized droplets of a coating solution.

Boyle et al, U.S. Pat. No. 5,925,381, describe the microencapsulation of oleophilic substances by forming an emulsion out of the oleophilic substance and a polymer, and then using heat setting and/or cross-linking of the polymer to encapsulate the oleophilic composition. This process is then repeated with a second polymer or third polymer, and with or without cross-linked via the same or different mechanism to further protect the oleophilic substance.

U.S. Pat. No. 4,353,962 discloses the in-flight encapsulation of materials for herbicidal, insecticidal and the like uses, for example, with film-forming polymers, in particular acrylic polymers from aqueous emulsion that may include a surfactant. The emulsion is spray dried onto the target in the form of a material encapsulated in a hardened x-linked acrylic encapsulating shell.

There is a need in the art for a microcapsule encapsulating active ingredients such as pharmaceuticals, herbicides, pesticides, flavors and fragrances, where the encapsulating shell is highly water soluble. Such a microcapsule would function to protect the encapsulated core material until placed into contact with an aqueous environment, when the active would be released instantly into the aqueous environment.

REPORTED DEVELOPMENTS

Water soluble microcapsules have been reported in the patent literature for many years for the preparation of storage stable flavors and fragrances using starch materials of one type or another as water soluble shell materials.

U.S. Pat. No. 3,455,838 discloses encapsulating lemon oil in a shell consisting of a dextrinized starch acid-ester of a substituted dicarboxylic acid. The encapsulate is prepared by mixing the lemon oil and an aqueous solution of the modified dextrin, passing it through a colloid mill, and spray drying the emulsion.

U.S. Pat. No. 3,499,962 discloses the encapsulation of water insoluble materials with a high amylose-containing starch material by mixing the insoluble material with an amylose solution at a temperature above 140 degrees F. and spray drying the mixture.

U.S. Pat. No. 5,370,881 discloses a micronized dispersion of flavor oil in a matrix of water soluble sucrose derivative such as isomalt. The matrix is formed in a flash flow process and the product is described as providing a rapid release of flavor.

U.S. Pat. No. 5,976,575 discloses encapsulated carotenoid oil prepared by emulsifying the oil with an aqueous solution of sugar, a starch encapsulating agent and an anti-oxidant, homogenizing the dispersion using a high pressure homogenizer and spray drying the resulting finely dispersed emulsion.

The use of other hydrophilic polymers such as cellulosic materials as the outer shell has also been described for encapsulated flavors as well as drug substances.

U.S. Pat. No. 3,664,963 discloses a lemon oil microcapsule encapsulated in a water soluble shell prepared from water soluble hydrophilic polymers including water soluble cellulosic compounds such as alkali cellulose, cellulose ethers and esters. The capsules are prepared from an oil in water emulsion of the lemon oil and polymer, which may include other ingredients including anti-oxidants and surfactants. The emulsion may be dispersed by a pressure homogenizer, and sprayed over polyethylene glycol to remove the water from the water soluble shell. The resulting capsules are coated with a layer of polyethylene glycol. The polyethylene glycol coated microcapsules are described as dissolving rapidly in cold water and which retain their fresh lemon flavor for an extended period of time in storage in the presence of air.

U.S. Pat. No. 4,540,602 discloses the encapsulation of scarcely soluble drugs with a water-soluble high molecular substance which can be one or a combination of materials such as cellulose derivatives such as hydroxypropyl methylcellulose, the sodium salt of carboxymethyl cellulose and other polymeric substances such as starches, gum arabic and the like. The drug and aqueous solution of high molecular weight substances are spray dried to form the microcapsules. The '602 patent states the emulsion may contain a surface active agent, such as polysorbate 80, HCO-60, an addition polymer of hydrogenated castor oil with ethylene oxide but that such use can result in hemolysis. Later on in the disclosure, the '602 patent discloses that small amounts of surfactants such as dioctyl sulfosuccinate, sucrose fatty acids and the like could be used because of their lack of hemolysis effect.

Other systems including the use of protein based materials and phospholipids have also been used as shell materials.

U.S. Pat. No. 5,601,760 discloses the microencapsulation of orange oil using a whey protein-based shell material which is dispersed in water with a starch or sugar, mixed with the orange oil, emulsified using a low and high speed homogenizer and spray dried.

U.S. Pat. No. 5,989,583 discloses liposomal composition described as quick dissolving powders prepared by homogenizing a solid fat and phospholipid and a surfactant, and spray drying the liposomal composition.

U.S. Pat. No. 5,317,004 discloses the microencapsulation of low melting herbicidal materials by admixing of a molten water insoluble core material with an aqueous solution of a water-soluble film forming polymer plus surfactant heated to a temperature that permits the core to remain molten and then spray drying the emulsion. Exemplary polymers include PVA, PVP and sodium carboxymethylcellulose. Exemplary surfactants include sodium dioctylsulfosuccinate.

While the methods of encapsulating water-insoluble materials with water soluble shell materials vary, there exists a need for an instant dissolvable microcapsule system that is storage stable for months under normal conditions, that may be prepared under conditions that minimize the oxidative and/or vapor loss impact on sensitive core materials such as flavors, fragrances, agricultural and drug substances.

SUMMARY OF THE INVENTION

The present invention relates to a water soluble microcapsule comprising a water insoluble core material and an encapsulating water soluble shell comprising a water soluble glucopyranosidyl material, at least two surfactants, and a water soluble cellulosic material.

The invention also relates to a process for the preparation of a water soluble microcapsule comprising subjecting an aqueous mixture of a water insoluble core material, a water soluble glucopyranosidyl material, a water soluble cellulosic material and an emulsifying composition to a pressure force to form an aqueous micro-emulsion, and removing the water from said micro-emulsion. This invention also relates to the water soluble microcapsule produced by the aforesaid process.

The primary advantages of the present invention include the preparation of a microcapsule that prevents environmental contact with an encapsulated water insoluble core material that is released from its encapsulating shell instantly on contact with an aqueous environment at ambient temperature. A further explanation of the unexpected advantages and benefits of the present invention are more fully described hereinbelow.

DETAILED DESCRIPTION

The following terms as defined hereinbelow are used throughout the present specification.

Encapsulation is applied to the formation from suitable materials of a shell that encloses a core material. The capsule that is formed may have a core material that is solid, liquid, gas, or a multi-phasic. Capsules having sizes ranging from approximately a micron to a few millimeters are generally referred to as microcapsules; although that term is not specifically defined in the literature. Capsules and/or microcapsules need not be uniformly spherical but may consist of irregularly-shaped objects such as those having a shell surrounding an irregular shaped solid crystalline core.

As used herein, the terms "shell" and "wall" are used interchangeably to denote the barrier surrounding the core material separating it from the environment. The shell or wall may likewise be complex having multiple walls of different composition. Thus, it is possible to have a first capsule having its own core and shell, which forms the core for a second capsule having a shell formed from the same or a different material.

The term "core material" is meant to define a material, preferably an organic material, which may comprise a single chemical compound or a mixture of chemical compounds and which is coated or encapsulated by the shell or wall material of the capsule. A capsule core may be a single solid crystal, a chemical compound, an emulsion, a liquid, a mixture of different solid materials or other suspensions, or it may be a combination of smaller capsules. A special embodiment of core materials include water insoluble compounds dissolved in a volatile organic medium, such as a low boiling point alcohol, or a low boiling point alkylene halide such as methylene chloride, or a non-volatile carrier oil, such as a low melting point fatty acid or fatty alcohols. Generally, any material that retains its shape and configuration in an aqueous medium, such as in the form of a suspended particle, colloid or emulsion, can be used as a core material.

The term "water insoluble" means that a material does not readily dissolve in water at room temperature. A material is considered water insoluble herein if a material is a mixture of chemical compounds, a minor fraction of which may be partially miscible in water.

The term "ambient temperature" means from about 5 degrees C. to about 35 degrees C. A most preferred ambient temperature is from about 15 degrees C. to about 25 degrees C.

The term "instantly released" means that substantially all of the core material is released into its environment within less than about 5 seconds. A preferred instant release time is less than about 3 seconds, with the most preferred time less than about 2 seconds.

The term "emulsifying composition" means a composition comprising one or more a non-toxic surfactants, preferably organic surfactants. The preferred emulsifying composition is capable of forming an aqueous emulsion in admixture with a water insoluble core material.

The term "pressure force" means an abrupt pressure change, a pressure shock wave, shear force, and/or cavitation resulting from the rapid change in pressure experienced by a composition subjected to a high pressure pumping or ultrasonic apparatus. The preferred pressure force is believed to occur in either or both of the high pressure compression chamber and during subsequent depressurization in baffle or shear chambers present in commercially available apparatus.

The term "spray drying" means the removal of water from an aqueous composition by forcing the composition through a narrow nozzle at high pressure into a volume of air or vacuum into which the water evaporates.

The microcapsule shell of the present invention is water soluble at ambient temperature conditions. In a preferred aspect, the microcapsule of the present invention dissolves instantly in water at ambient temperature thereby releasing its core material into the aqueous environment.

The advantages of the present invention to the food and beverage industry include the ability to provide flavors and fragrances that may be mixed in water without heating and that release their encapsulated flavors or fragrances immediately. The most preferred microcapsule dissolves instantly in cold water, that is at a temperature slightly above the freezing point, with only modest stirring. A further preferred water soluble microcapsule comprises an aromatic core material, preferably an organic composition including one or more compounds that have a low vapor pressure and are volatile at ambient temperature and pressure of about 1 atmosphere, the vapor pressure of which suppressed at ambient temperature.

The advantages of the present invention extend into many industries including pharmaceuticals, where active ingredients capable of mucosal absorption such as nitroglycerin may be formulated as microcapsules and compressed into tablets for oral administration, or used as powders for nasal or bronchial inhalation administration. Upon contact with the moist body temperature mucosa in the mouth, nasal passages or aveoli of the lung, the active ingredient would instantly be released for absorption into the patient's bloodstream Other industries also could benefit from the present invention. For example, herbicides and pesticides could be formulated such that they are applied to vegetation as dry granules that release on application of water, either by nature's rain or the hand of man.

The present microcapsule comprises a core material, preferably an organic material, that is water insoluble or only slightly water soluble, and that is encapsulated or coated with a water soluble shell comprising a matrix of a water soluble glucopyranosidyl compound and an emulsifying composition.

"Glucopyranosidyl material" means a composition including a compound containing a glucopyranosidyl ring structure, and mixtures thereof. A special embodiment of the glucopyranosidyl materials comprises the dissacharrides including the naturally occurring disaccharides and the enantiomers thereof; while another special embodiment comprises the enzymatically and/or chemically modified derivatives of the naturally occurring disaccharides, including hydrogenated, methylated, oxidized, acetylated, aminated and enzymatically rearranged derivatives thereof.

"Disaccharide" as used herein means an organic dimeric material considered as derived from the hydrolysis of polysaccharides that are branched or straight-chained, looped or coiled polymers of repeating monosacharride units formed from aldose or ketoses by condensation polymerization. An exemplary polysaccharide derived from hexoses has the general formula $(C6H10O5)n$. Disaccharides are glucopyranosidyl compounds made up of two monosacharride units. The trivial names of exemplary naturally derived disaccharides are maltose, sucrose, lactose, cellobiose, trehalose, gennobiose, isomaltose, melibiose, prieverose, and rutinose.

Exemplary glycopyranosidyl compounds that comprise the derivatives of the natural disaccharides, include maltobionic acid, octa-O-methyl-D-maltobionic acid, cellubiose octaacetate, lactobionic acid, isomaltulose(6-O-D-glucopyranosido-D-fructose), 1,2;4,5-di-O-isopropylidene-beta-D-fructopyranose, 1,2:5,6-di-O-isopropylidene-alpha-D-glucofurnaose, 2,3:5,6-di-O-isopropylidene-alpha-D-mannofuranose, lactitol monohydrate; (+)-turanose, kojibiose, lactosamine, lactosediamine, laminarabiose, ngerose, sopharose, trehalosamine, alpha-D-glucopyranosyl-1,1-D-mannitol and alpha-D-glucopyranosyl-1,6-D-sorbital, and isomalt, an equimolar mixture of alpha-D-glucopyranosyl-1,1-D-mannitol and alpha-D-glucopyranosyl-1,6-D-sorbital, among others.

A particularly preferred subgroup of these derivatives comprises the compounds based on the 1-O- or 6-O-polyhydroxyalkylethers of glucopyranoside having a alkyl group containing about 5 to 6 carbon atoms ring and a total of about 12 to 14 carbon atoms, and wherein the side chain comprises about 4 to about 6 hydroxyl groups and optionally, about 1 to 2 carbonyl groups. The disaccharide derivatives may also be described as the result of the 1-O- or 6-O ether linkage of glucose to a conventional sugar alcohol, sugar carboxylic acid, or sugar dicarboxylic acid, examples of which include hexitols such as glucitol, galactitol, mannitol and gulitol; pentitols such as arabinitol, ribitol and xylitol; tetritols such as threitol and erythritol or glycerol, and derivatives of such sugar alcohols can be mono- or multiply-desoxygenated sugar alcohols such as L-rhamnitol, ribonic acid, gluconic acid and gulonic acid, and tartaric acid, galactaric acid and glucaric acid.

These sugar alcohols and sugar carboxylic acids can be present in the D- or L-form or as racemates, with the naturally occurring form or the form which corresponds to the basic, naturally occurring sugar being preferred.

The most preferred glucopyranosidyl materials are 1-polyhydroxyalkylethers of glucopyranoside that may be prepared by the selective Raney nickel hydrogenation of the corresponding reducing disaccharides, which comprise all the naturally occurring disaccharides excluding sucrose and trehalose, and include the enzymatically rearranged products of the non-reducing disaccharides such as sucrose and trehalose. A special embodiment of this invention utilizes as the glucopyranosidyl material, an equimolar mixture of alpha-D-glucopyranosyl-1,1-D-mannitol and alpha-D-glucopyranosyl-1,6-D-sorbital, sold under the tradename Isomalt.

A preferred microcapsule includes from about 2 to about 60 weight percent of said disaccharide or derivative thereof and about 1 to about 35 percent, or more preferably from about 10 to about 30 percent, of said core material. A special embodiment of the microcapsule includes about 50 percent of said disaccharide and about 20 percent of said core material. A most preferred microcapsule includes about 20 percent of said disaccharide and about 10 percent of said core material. The emulsifying composition comprises about 0.5 to about 3 percent of the dry microcapsule by weight, while a preferred microcapsule includes the emulsifying composition in about 1 percent by weight.

The emulsifying composition preferably includes at least two non-toxic surfactants. There are a great many surfactants, anionic, cationic, non-ionic or amphoteric in character, which may be employed, depending upon the hydrophobic substance to be employed. Among the well-known surfactants useful in the process of the present invention are the sorbitan esters of fatty acids having 10 to 22 carbon atoms; polyoxyethylene sorbitan esters of $C_{10}$ to $C_{22}$ fatty acids having up to 80% ethylene oxide; polyoxyethylene sorbitol esters of $C_{10}$ to $C_{22}$ fatty acids, polyoxyethylene derivatives of fatty phenols having 6 to 20 carbon atoms and up to 80% ethylene oxide; fatty amino and amido betaines having 10 to 22 carbon atoms; fatty alcohols of 5 to 16 carbon atoms, polyoxyethylene condensates of $C_{10}$ to $C_{22}$ fatty acids or fatty alcohols having up to 80% ethylene oxide; polyoxyethylene-polyoxypropylene block polymers; ionic surfactants such as the alkylaryl sulfonates of 6 to 20 carbons in the alkyl group; $C_{10}$ to $C_{22}$ fatty acid soaps; $C_{10}$ to $C_{22}$ fatty sulfates; $C_{10}$ to $C_{22}$ alkyl sulfonates; $C_{10}$ to $C_{22}$ fatty amine oxides; fatty imidazolines of $C_6$ to $C_{22}$ carbon atoms; fatty amido sulfobetaines having 10 to 22 carbon atoms; quaternary surfactants such as the fatty ammonium compounds having 10 to 22 carbon atoms; $C_{10}$ to $C_{22}$ fatty morpholine oxides, alkali metal salts of carboxylated ethoxylated $C_{10}$ to $C_{22}$ alcohols having up to 80% E.O., ethylene oxide condensates of $C_{10}$ to $C_{22}$ fatty acid monoesters of glycerins having up to 80% E.O. and the mono- or diethanol amides of $C_{10}$ to $C_{22}$ fatty acids, etc. As is well known in the field of surfactants, the counter ion in the case of anionic surfactants may be any of the alkali metals, ammonia, or substituted ammonias such as trimethylamine or triethanol amine. Usually ammonium, sodium and potassium are preferred. In the case of cationic surfactants, the counter ion is usually a halide, sulfate or methosulfate, the chlorides being the most common industrially available compounds. The foregoing compounds have been described with particular reference to fatty derivatives. It is the fatty moiety usually forming the lipophilic moiety. A common fatty group is an alkyl group of natural or synthetic origin. In most instances, the alkyl group may be replaced by the corresponding ethyleneically saturated group having one or more ethylene linkages such as commonly occur in nature. Common unsaturated groups are oleyl, linoleyl, decenyl, hexadecenyl, dodecenyl, etc. In appropriate cases, as known in the art, the alkyl group may be cyclic, i.e., cycloalkyls, or may be straight or branched chain.

Among the surfactants found particularly useful in accordance with the present invention are nonylphenol-polyoxyethylene condensates, the sorbitan and sorbital mono esters $C_{12}$ to $C_{18}$; fatty acids, and their ethylene oxide condensates.

Other representative primary surfactants are: sorbitol monolaurate-ethylene oxide condensates; sorbitol monomyristate-ethylene oxide condensates; sorbitol monostearate-ethylene oxide condensates; dodecylphenol-ethylene oxide condensates; myristylphenol-ethylene oxide condensates; octylphenyl-ethylene oxide condensates; stearylphenol-ethylene oxide condensates; lauryl alcohol-ethylene oxide condensates; stearyl alcohol-ethylene oxide condensates; secondary alcohol-ethylene oxide condensates such as commercial $C_{14}$ to $C_{15}$ secondary alcohols condensed with ethylene oxide (commercially available as "Tergitol"); decyl amino betaine; coco amino betaine; cetyl amino betaine; coco amido betaine; coco amido sulfobetaine; oleyl amido betaine, coco imidazoline; coco sulfoimidazoline, cetyl imidazoline, 1-hydroxyethyl-2-heptadecenyl imidazoline; 1-hydroxyethyl-2-mixed hepta-decenyl heptadecadienyl imidazoline; n-coco morpholine oxide; decyl dimethyl amine oxide; coco amido dimethyl amine oxide; sorbitan tristearate condensed with ethylene oxide; sorbitan trioleate condensed with ethylene oxide; sorbitan trioleate; sodium or potassium dodecyl sulfate; sodium or potassium stearyl sulfate; sodium or potassium dodecyl benzene sulfonate; sodium or potassium stearyl sulfonate; triethanol amine salt of dodecyl sulfate; trimethyl dodecyl ammonium chloride; trimethyl stearyl ammonium methosulfate; polyoxyethylene/polyoxypropylene block polymers having 10%–80% ethylene oxide (by weight) and a molecular weight of 900 to 16,000; sodium laurate; sodium or potassium myristate; and sodium or potassium stearate.

The polyoxyethylene condensates are particularly convenient in this invention because the HLB of the polyoxyethylene surfactants can be made to vary in a regular fashion depending upon the amount of ethylene oxide condensed onto the hydrophilic portion of the molecule. This facilitates the selection of a primary surfactant having the correct HLB.

While the use of a single surfactant can, in many instances, be sufficient to serve as the primary surfactant in accordance with the process of this invention, the use of a mixed primary surfactant is particularly important in achieving the quick dissolving aspects of the present invention. When selecting a primary or secondary surfactant from a series of polyoxyethylene condensates of nonylphenol, the commercially available condensates may contain, for example, 1, 4 or 9 ethylene oxide units condensed with the nonylphenol. In such a sequence of compounds, a mixture of one part of nonylphenol.multidot.4EO and 1 part nonylphenol.multidot.9EO may prove more effective as the primary surfactant than either nonylphenol.multidot.4EO or nonylphenol.multidot.9EO alone.

As indicated above, the suitability for the primary surfactant for any given oil phase may be tested by a simple procedure. Most conveniendy, a series of related surfactants are considered, such as a series of alkyl alcohols, condensed with varying amounts of ethylene oxide. A small quantity, for example, ¼ gram of a gram of the putative primary surfactant, is dissolved in several millilters (for example 10 ml) of the oil phase to be dispersed. Where the oil phase to be dispersed is a solution of hydrophobic substance to be dispersed in a solvent, the test should be carried out on that solution. If a clear solution results, a primary surfactant, from the series having a higher HLB (i.e., more ethylene oxide) is selected and the test repeated. When the new surfactant has a sufficiently high HLB, addition of the surfactant will result in a cloudy suspension rather than a clear solution. In this manner, a surfactant (or surfactant mixture) for the oleophilic phase is selected having an HLB not substantially lower than required to render the surfactant soluble in the oil phase.

In practice the surfactants of a series differ by discrete values of HLB. Therefore, in the selection of a surfactant the practical HLB of the first and second members of a series may be too high, and the HLB of the fourth and fifth members of the series will be too low. The third member would be selected, in that case, even though it may not be completely soluble in the oleophilic phase as shown by the simple test.

The hydrophilic-lipophilic balance of a compound is a concept well established in the surfactant field, and generally is used to describe the relative affinities of the hydrophilic and lipophilic moieties that make up the amphoteric molecule. A substance having a high HLB usually has a relatively strong polar group readily soluble in water and a relatively weak lipophilic group. Typically, such substances are soluble in water but not in oils. Conversely, a substance with a low HLB is usually dominated by a large lipophilic group and is soluble in oils. While there have been some attempts to define an HLB scale on the basis of arbitrary solvents, it more practical for purposes of the present invention to test the HLB of the amphoteric surfactants to be used with the particular oil and water phases to be emulsified.

The preferred surfactants useful in the practice of the present invention include a combination of at least one fatty acid ester of a polyoxyalkyleneoxide as the first surfactant, and a fatty acid ester of a monosacharride as the second surfactant.

The emulsifying composition comprises about 5–30 percent of the first polyoxyalkyleneoxide surfactant and about 70 to about 95 percent of the second monosacharride surfactant. The most preferred surfactants useful in the present invention are polysorbate 60, also known as polyoxyethylene 20 sorbitan monostearate, sold under the mark, Tween 60 and sorbitan monostearate, sold under the trademark, Span 60, both of which are commonly used in the food and pharmaceutical industry. The most preferred ratio of polymeric surfactant to monosacharride surfactant is about 1 to about 9.

The preferred microcapsule also comprises in its shell a cellulosic material that facilitates the preferred method of drying the composition, for example by spray drying. The cellulosic material is included in an amount from about one to about 15 percent of the weight of the microcapsule, while the preferred weight is about two to about ten percent. The preferred cellulosic materials include hydroxyl alkyl alkylcellulose and the metal salts of a carboxyalkylcellulose. The most preferred cellulosic materials include hydroxyl propyl methylcellulose and the metal salts of carboxymethylcellulose. The most preferred cellulosic material is the sodium salt of carboxymethylcellulose.

The disaccharide material, the cellulosic material and the emulsifying composition surfactants are all preferably nontoxic, generally accepted as safe for ingestion and pharmaceutically acceptable.

The microcapsule is produced by subjecting a aqueous mixture of the core material, water soluble disaccharide material, emulsifying composition and preferably the spray enhancer to an abrupt pressure change, preferably followed by the removal of the aqueous medium by spray drying.

The mixing of the shell and core material to form a dispersion, or a micro-dispersed or homogenized state, may be accomplished by any of the conventionally known apparatuses including those known as batch mixers, static mixers, motionless mixtures, homogenizer and fluidization equipment. The core and shell materials should be adequately mixed to form a fairly homogenous dispersion of the core and shell materials in the aqueous medium. The micro-dispersion is, on a macroscopic level, generally homogeneous, though not perfectly so.

In order to form capsules by the method of this invention, a homogenized dispersion of core and shell material in an aqueous medium is passed through a pressure pulse apparatus, which can be a microfluidizer, ultra-homogenizer or other high pressure pulse apparatus that impart an abrupt pressure pulse, high shear and/or cavitation forces to the mixture sufficient to promote microencapsulation of the core material. The application of the pressure-pulse may be accomplished by means of a hydraulic pump as described in U.S. Pat. No. 5,271,881, herein incorporated by reference. A preferred apparatus includes a baffle chamber through which the suspension is forced and in which shear and/or cavitation forces impact the suspension.

The function of the pressure pulse apparatus used to form the microcapsules is described briefly as follows. The dispersion of core and shell material is placed in the pump reservoir, and may be conveniently fed under the force of gravity to the open inlet valve permitting the dispersion of core and shell material to flow into the compression chamber. The inlet valve is then closed and high pressure air supplied to a pneumatic motor that drives the piston down into the compression chamber thereby applying an abrupt pressure change to the dispersion of core and shell material contained therein. One or several stroke cycles, consisting of a compression followed by a rarefaction stroke, of the piston may be applied to the dispersion of core and shell in the compression chamber before the exit valve is opened. The impact and withdrawal of piston upon the virtually non-compressible material in compression chamber produces abrupt pressure changes resulting in pressure shock waves, shear forces, and, perhaps, cavitation within the liquid medium. After the dispersion is subjected to these forces, exit valve is opened and the liquid medium flows out of compression chamber into capsule discharge line that leads to the baffle chamber.

A preferred embodiment of the pressure pulse apparatus uses a baffle chamber comprising a section of decreased diameter leading to an inner chamber having baffles that interrupts and delays and increases the turbulence of the flow of the capsule containing mixture.

The baffle chamber is sometimes called the "stabilization tube". As the pump forces the capsule mixture through the stabilization tube, the fluid encounters a reduced diameter channel that increases the velocity of the fluid.

The pulse-pressure treated mixture is then spray dried to complete the encapsulation process and recover the water soluble microcapsules. The following example describes one embodiment of the present invention is more detail.

EXAMPLE 1

Water Soluble Microencapsulated Orange Oil

| Formulation: | |
| --- | --- |
| 1-Isomalt | 80 g |
| 2-Blanose 7LF (NaCMC) | 10 g |
| 3-Tween 60 | 1.8 g |
| 4-Span 60 | 0.2 g |
| 5-Distilled. Water | 400 ml |
| 6-Orange Oil Flavor | 40 g |

Procedure:

Add Blanose (brand name of sodium carboxymethylcellulose) gradually to the distilled water while mixing until the mixture clarifies. Add a mixture of Tween 60 and Span 60 to the clarified Blanose solution and continue mixing for about 20 minutes. Add the Isomalt to the mixture and continue to mix for a minimum of another twenty minutes. Add the orange oil flavor and homogenize the mixture for another five minutes. Pass the homogenized orange oil mixture once through the Beta hydraulic pressure pump at 90 psi input air pressure. Spray dry the pressure treated mixture at 110 degrees C., 2.0 kgf/cm$^2$ (atomizing pressure), 0.34 cubic ft air flow, set at pump speed no. 2. The pressure measured before the baffle chamber is about 8,000 psi.

The spray dried microcapsules of orange oil are essentially odorless. When about 0.1 gram of microcapsules is added to about 10 ml of cold tap water the capsules disappeared and releases the orange oil in less than about three seconds at room temperature with gentle swirling. Furthermore, when subjected to stability testing, after 65 days, the limonene oxide content of the encapsulated orange oil increased only from 0.3 mg/g of orange oil to 0.9 mg/g of orange oil. The best comparative microcapsules prepared by spray drying orange oil with the encapsulating agent, N-Lok™, exhibit increases in limonene oxide content from about 0.3 mg/g to about 2.9 to 3.6 mg/g in 65 days.

EXAMPLE 2

Water Soluble Microencapsulated Orange Oil (Formulation 2)

| Formulation: | |
| --- | --- |
| 1-Sucrose | 75 g |
| 2-Blanose 7LF (NaCMC) | 14 g |
| 3-Tween 60 | 2.7 g |
| 4-Span 60 | 0.3 g |
| 5-Distilled. Water | 400 ml |
| 6-Orange Oil Flavor | 40 g |

Procedure:

Add Blanose (brand name of sodium carboxymethylcellulose) gradually to the distilled water while mixing until the mixture clarifies. Add a mixture of Tween 60 and Span 60 to the clarified Blanose solution and continue mixing for about 20 minutes. Add the sucrose to the mixture and continue to mix for a minimum of another twenty minutes. Add the orange oil flavor and homogenize the mixture for another five minutes. Pass the homogenized orange oil mixture once through the Beta hydraulic pressure pump at 90 psi input air pressure. Spray dry the pressure treated mixture at 110 degrees C., 2.0 kgf/cm$^2$ (atomizing pressure), 0.34 cubic ft air flow, set at pump speed no. 2. The pressure measured before the baffle chamber is about 8,000 psi.

The spray dried microcapsules of orange oil are essentially odorless. When about 0.1 gram of microcapsules is added to about 10 ml of cold tap water the capsules disappeared and released the orange oil in less than about five seconds at room temperature with gentle swirling. The formulation has essentially similar stability properties as Example 1.

EXAMPLE 3

Nifedipine Drug

| Formulation: | |
| --- | --- |
| 1-Sucrose | 50 g |
| 2-Blanose 7LF (NaCMC) | 12 g |
| 3-Tween 60 | 2.7 g |
| 4-Span 60 | 0.3 g |
| 5-Distilled. Water | 400 ml |
| 6-nifedipine powder | 14 g |
| Methylene Chloride | 100 ml |

Procedure:

Add a mixture of Tween 60 and Span 60 gradually to the distilled water while mixing for about 30 minutes. Add Blanose (brand name of sodium carboxymethylcellulose) to the surfactant solution and continue mixing for about 30 minutes. Add the sucrose to the mixture and continue to mix for a minimum of another ten minutes. Add a solution of the nifedipine in methylene chloride (100 ml) and mix for another five minutes. Pass the emulsified mixture twice through the Beta hydraulic pressure pump at 90 psi input air pressure. Spray dry the pressure treated mixture at an inlet temperature of 110 degrees C., an outlet temperature of 55 degrees C., and an atomizing pressure of 2.5 kgf/cm$^2$.

EXAMPLE 4

Nifedipine Drug

| Formulation: | |
| --- | --- |
| 1-Sucrose | 156 g |
| 2-Blanose 7LF (NaCMC) | 25 g |
| 3-Tween 60 | 4.5 g |
| 4-Span 60 | 0.5 g |
| 5-Distilled. Water | 800 ml |
| 6-nifedipine powder | 14 g |

Procedure:

Add a mixture of Tween 60 and Span 60 gradually to the distilled water while mixing for about 30 minutes. Add Blanose (brand name of sodium carboxymethylcellulose) to the surfactant solution and continue mixing for about 30 minutes. Add the sucrose to the mixture and continue to mix for a minimum of another ten minutes. Add the nifedipine and mix for another five minutes. Pass the emulsified mixture twice through the Beta hydraulic pressure pump at 90 psi input air pressure. Spray dry the pressure treated mixture at an inlet temperature of 300 F for inlet temperature and 225 F for outlet temperature, and an atomizing air pressure set at 80 psi.

The outer shell of the spray dried microcapsules of nifedipine dissolve instantly in cold water in less than about five seconds, producing water insoluble fine crystals of nifedipine.

I claim:

1. A process for the preparation of a water soluble microcapsule comprising subjecting an aqueous mixture, consisting essentially of a water insoluble core material, a water soluble glucopyranosidyl material, a chemically modified water soluble cellulosic material and an emulsifying composition, to a pressure force to form an aqueous micro-emulsion, removing the water from said micro-emulsion, and thereby forming a microcapsule comprising about 20 to about 78 weight percent of said glucopyranosidyl material, and about one to about 15 weight percent of said cellulosic material, said microcapsule being capable of instantly releasing said core material on contact with water at ambient temperature.

2. A process according to claim 1 wherein said water is removed by spray drying said micro-emulsion to form said microcapsule.

3. A process according to claim 1 wherein said water soluble glucopyranosidyl material is a naturally derived disaccharide.

4. A process according to claim 1 wherein said glucopyranosidyl material is a polyhydroxyalkyloxy ether of a glucopyranoside.

5. A process according to claim 1 wherein said glucopyranosidyl material is isomalt or sucrose.

6. A process according to claim 1 wherein said mixture further comprises a spray drying enhancer which is a chemically modified water soluble cellulosic material.

7. A process according to claim 1 wherein said cellulosic material is a hydroxy alkyl alkylcellulose or a metal salt of a carboxyalkylcellulose.

8. A process according to claim 7 wherein said material is a hydroxypropyl methylcellulose or a metal salt of a carboxymethylcellulose.

9. A process according to claim 1 wherein said emulsifying composition comprises about 0.5 to about 3 percent of said microcapsule by weight.

10. A process according to claim 9 wherein said emulsifying composition comprises about 1 percent of said microcapsule by weight.

11. A process according to claim 9 wherein said emulsifying composition comprises about 5 to about 30 percent of a first polymer surfactant and about 70 to about 95 percent of a second monosacharride surfactant.

12. A process according to claim 11 which produces a water soluble microcapsule that dissolves in water at room temperature in less than about three seconds.

13. A water soluble microcapsule produced in accordance with claim 1.

14. A water soluble microcapsule produced in accordance with claim 1 and which comprises an core comprising organic compounds possessing low vapor pressure, the release of which vapor is masked at room temperature.

15. A process according to claim 1 wherein said microcapsule contains about 20 percent of said glucopyranosidyl material and about 10 percent of said core material.

16. A process according to claim 1 wherein said abrupt pressure is applied for less than a second at a pressure of from about 2,000 psi to about 20,000 psi.

17. A process for the preparation of a water soluble microcapsule, comprising (a) subjecting an aqueous mixture to a pressure force to form an aqueous micro-emulsion;

(b) wherein said aqueous mixture comprises water, a water insoluble core material, a water soluble glucopyranosidyl material, and an emulsifying composition comprising a first polymeric surfactant and a second monosaccharide surfactant; and (c) removing said water from said micro-emulsion to form said microcapsule;

(d) wherein said microcapsule comprises about 0.5 to about 3 weight percent of said emulsifying composition comprising about 5 to about 30 percent of said first surfactant and about 70 to about 95 percent of said second surfactant; and, wherein said microcapsule is capable of dissolving in water at ambient temperature in less than about three seconds.

18. A process according to claim 17 wherein said mixture further comprises a chemically modified water soluble cellulosic material.

19. A process according to claim 18 wherein said water is removed by spray drying said micro-emulsion to form said microcapsule.

20. A process according to claim 17 wherein said water soluble glucopyranosidyl material is a naturally derived disaccharide.

21. A process according to claim 17 wherein said glucopyranosidyl material is a polyhydroxyalkyloxy ether of a glucopyranoside.

22. A process according to claim 17 wherein said glucopyranosidyl material is isomalt or sucrose.

23. A process according to claim 17 wherein said cellulosic material is a hydroxy alkyl alkylcellulose or a metal salt of a carboxyalkylcellulose.

24. A process according to claim 22 wherein said material is a hydroxypropyl methylcellulose or a metal salt of a carboxymethylcellulose.

25. A process according to claim 17 wherein said surfactants comprise about one percent of said microcapsule by weight.

26. A process according to claim 17 which produces a water soluble microcapsule that dissolves in water at room temperature in less than about three seconds.

27. A process according to claim 18 wherein said microcapsule contains about 20 to about 78 weight percent of said glucopyranosidyl material and about one to about 15 weight percent of said cellulosic material.

28. A process according to claim 17 wherein said pressure is applied for less than a second at a pressure of from about 2,000 psi to about 8,000 psi.

29. A water soluble microcapsule produced in accordance with claim 17.

30. A water soluble microcapsule of claim 29, wherein said core material comprises a flavor, fragrance, agricultural or drug substance containing organic compounds sensitive to oxidation, and is capable of minimizing oxidative and/or vapor loss of said sensitive organic compounds and is storage stable for months under normal conditions.

* * * * *